(12) United States Patent
Pelissier et al.

(10) Patent No.: US 8,088,070 B2
(45) Date of Patent: Jan. 3, 2012

(54) HAND-HELD ULTRASOUND IMAGING DEVICE HAVING REMOVABLE TRANSDUCER ARRAYS

(75) Inventors: Laurent Pelissier, Vancouver (CA); Kris Dickie, Chilliwack (CA); Kwun-Keat Chan, Vancouver (CA)

(73) Assignee: Ultrasonix Medical Corporation, Richmond (CA)

( * ) Notice: Subject to any disclaimer, the term of this patent is extended or adjusted under 35 U.S.C. 154(b) by 544 days.

(21) Appl. No.: 12/188,189

(22) Filed: Aug. 7, 2008

(65) Prior Publication Data

US 2009/0043204 A1 Feb. 12, 2009

Related U.S. Application Data

(60) Provisional application No. 60/955,325, filed on Aug. 10, 2007.

(51) Int. Cl.
*A61B 8/00* (2006.01)
(52) U.S. Cl. .................. 600/446; 600/459; 600/463
(58) Field of Classification Search .................. None
See application file for complete search history.

(56) References Cited

U.S. PATENT DOCUMENTS

| | | | |
|---|---|---|---|
| 4,106,492 A * | 8/1978 | Schuette et al. ............ 600/446 |
| 5,295,485 A | 3/1994 | Shinomura et al. | |
| 5,590,658 A | 1/1997 | Chiang et al. | |
| 5,617,864 A * | 4/1997 | Stouffer et al. ............ 600/459 |
| 5,722,412 A | 3/1998 | Pflugrath et al. | |
| 5,817,024 A | 10/1998 | Ogle et al. | |
| 6,106,472 A | 8/2000 | Chiang et al. | |
| 6,139,496 A * | 10/2000 | Chen et al. ............ 600/437 |
| 6,203,498 B1 | 3/2001 | Bunce et al. | |
| 6,251,073 B1 | 6/2001 | Imran et al. | |
| 6,425,870 B1 * | 7/2002 | Flesch ............ 600/459 |
| D461,895 S * | 8/2002 | Barnes et al. ............ D24/158 |
| 6,488,625 B1 * | 12/2002 | Randall et al. ............ 600/437 |
| 6,569,102 B2 | 5/2003 | Imran et al. | |
| 6,638,226 B2 | 10/2003 | He et al. | |
| 6,953,433 B2 | 10/2005 | Kerby et al. | |
| 7,115,093 B2 | 10/2006 | Halmann et al. | |
| 7,221,972 B2 | 5/2007 | Jackson et al. | |
| 2005/0251035 A1 * | 11/2005 | Wong et al. ............ 600/437 |

* cited by examiner

*Primary Examiner* — Unsu Jung
*Assistant Examiner* — Lawrence Laryea
(74) *Attorney, Agent, or Firm* — Oyen Wiggs Green & Mutala LLP

(57) ABSTRACT

A hand-held ultrasonic imaging device is provided with a removable transducer array. The imaging device has a housing, a display on the housing, and a transducer assembly including a transducer array detachably coupled to the housing. The imaging device may detect the type of transducer array that is coupled to the housing and select a corresponding functional mode for the transducer array. The transducer array may be coupled at different angles to the housing. The transducer array may be coupled to the housing by a pivotable swivel connector.

19 Claims, 5 Drawing Sheets

HAND-HELD ULTRASOUND IMAGING DEVICE HAVING REMOVABLE TRANSDUCER ARRAYS

CROSS-REFERENCE TO RELATED APPLICATION

This application claims priority from U.S. patent application No. 60/955,325 filed 10 Aug. 2007 and entitled HAND-HELD ULTRASOUND IMAGING DEVICE HAVING REMOVABLE TRANSDUCER ARRAYS. This application claims the benefit under 35 U.S.C. §119 of U.S. patent application No. 60/955,325 filed 10 Aug. 2007 and entitled HAND-HELD ULTRASOUND IMAGING DEVICE HAVING REMOVABLE TRANSDUCER ARRAYS which is hereby incorporated herein by reference.

TECHNICAL FIELD

This invention relates to ultrasound imaging devices. Particular embodiments of the invention relate to hand-held ultrasound imaging devices.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

In FIG. 3A, the transducer assembly has elements arranged in a convex array. In FIG. 3B, the transducer assembly has elements arranged in a linear array. In FIG. 3C, the transducer assembly has elements arranged to provide a phased array.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The features as described herein may be combined in any suitable combinations with the features described in the commonly-owned US provisional patent applications entitled:

HAND-HELD ULTRASOUND SYSTEM HAVING STERILE ENCLOSURE (application No. 60/955,327);
HAND-HELD ULTRASOUND IMAGING DEVICE HAVING RECONFIGURABLE USER INTERFACE (application No. 60/955,328);
POWER MANAGEMENT IN PORTABLE ULTRASOUND DEVICES (application No. 60/955,329);
WIRELESS NETWORK HAVING PORTABLE ULTRASOUND DEVICES (application No. 60/955,331); and
HANDHELD ULTRASOUND IMAGING SYSTEMS (application No. 60/977,353)

all of which are hereby incorporated herein by reference. The features as described herein may also be combined in any suitable combinations with the features described in the commonly-owned US non-provisional patent applications which are filed on the same day as the instant application and entitled:

HAND-HELD ULTRASOUND SYSTEM HAVING STERILE ENCLOSURE (claiming priority from application No. 60/955,327);
HAND-HELD ULTRASOUND IMAGING DEVICE HAVING RECONFIGURABLE USER INTERFACE (claiming priority from application No. 60/955,328);
POWER MANAGEMENT IN PORTABLE ULTRASOUND DEVICES (claiming priority from application No. 60/955,329);
WIRELESS NETWORK HAVING PORTABLE ULTRASOUND DEVICES (claiming priority from application No. 60/955,331); and
HANDHELD ULTRASOUND IMAGING SYSTEMS (claiming priority from application No. 60/977,353)

all of which are hereby incorporated herein by reference.

Figure 1:
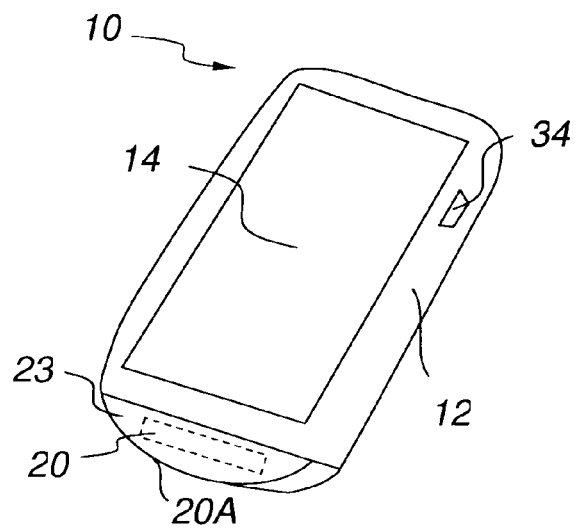
FIG. 1 shows a hand-held ultrasonic apparatus according to one embodiment of the invention.

This invention provides hand-held ultrasound imaging devices that have detachable ultrasound transducer arrays. FIG. 1 shows an overview of an example ultrasound device 10 according to one particular embodiment of the invention. Device 10 comprises a housing 12 bearing a display 14. A transducer array 20 is connected to electronic circuitry within housing 12. The electronic circuitry controls the generation and reception of ultrasound signals by way of transducer array 20 and the processing of received signals to produce ultrasound images. The images may be displayed on display 14. Device 10 may be self-contained, providing all of the necessary circuitry to obtain and display ultrasound images on display 14. Device 10 is suitably small enough to be hand carried, and preferably is small enough to keep in a person's pocket. For example, housing 12 may have dimensions of approximately 10 cm×8 cm×2 cm. Device 10 may weigh less than 10 pounds (approximately 4.5 kg).

Figure 2:
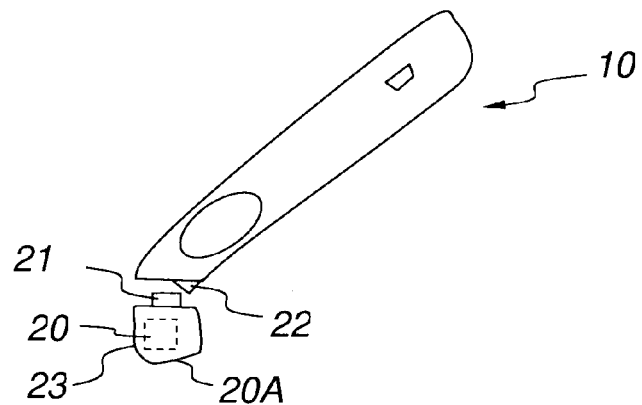
FIG. 2 shows the apparatus of FIG. 1 with the removable transducer array unplugged from the housing of the apparatus.

In one embodiment of the invention, as shown in FIG. 2, transducer array 20 is detachable from housing 12. In the illustrated embodiment, transducer array 20 is part of a transducer assembly 23 that comprises a connector 21 that can be coupled to a mating connector 22 on device 10. Connectors 21 and 22 may comprise multi-pin electrical connectors, for example. A user can replace a damaged transducer array 20 by unplugging the transducer assembly 23 that carries the damaged transducer array 20 and plugging in a transducer assembly 23 having a new transducer array 20. A user can change from one type of transducer array 20 to another type of transducer array for some purpose (for example, for changing to another type of ultrasound imaging or monitoring) by unplugging the transducer assembly 23 that carries the first transducer array 20 and plugging in a transducer assembly 23 carrying a different transducer array 20.

Figure 3A:
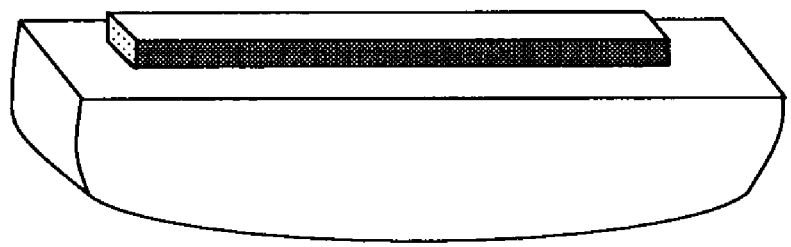
FIGS. 3A to 3C show various removable transducer arrays that may be provided in embodiments of the invention.
Figure 3B:
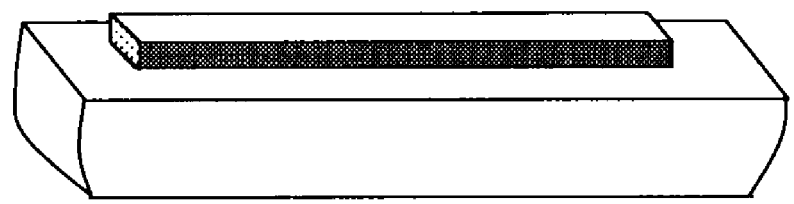
Figure 3C:
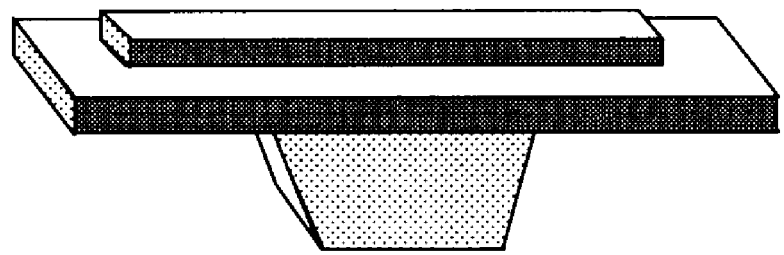

In some embodiments, device 10 is customized to perform a specific imaging function or imaging functions. In such embodiments, optionally, device 10 may detect the type of transducer array 20 currently plugged into it and selects a functional mode which matches the type of transducer array 20 that is plugged in. Changing to different functional modes can be performed by selecting and plugging in a transducer array 20 appropriate to the desired functional mode. In some embodiments, device 10 may have suitable user controls 34 provided on a user interface which allow a user to select a functional mode or type of transducer array 20 which is plugged in. FIGS. 3A to 3C illustrate various transducers that may be used for different functional modes. A device 10 may be supplied with several such transducers that are all attachable to housing 12 of device 10.

A transducer array 20 may comprise one or more electrical connections, circuit elements, structural features or indicia detectable by device 10 that identify the transducer array 20. Device 10 may be configured to automatically set up to operate in a functional mode associated with the current transducer array 20 when the transducer array 20 is plugged in and detected by device 10. In some embodiments, the transducer assembly 23 may comprise a memory comprising configuration data (which may include parameters and/or software instructions) that in whole or in part define a functional mode associated with the transducer array 20. For example, the configuration data may comprise data for configuring a field-programmable gate array (FPGA), if device 10 is so-equipped, to control the transducer array 20 to emit appropriate ultrasound signals and/or to process ultrasound data received by way of the transducer array 20. The configuration data may comprise other types of data for defining user interface controls of device 10, user manual information, etc.

For certain types of ultrasound imaging it can be desirable to hold the housing 12 at specific angles relative to the subject. In some embodiments, transducer array 20 is coupled to housing 12 at a specific angle, a, relative to the active face 20A of transducer array 20. Different transducer arrays may be provided for which the angle α is different. A user can adapt ultrasound device 10 to be operated at a desired angle α relative to the surface of a subject by selecting and plugging in a transducer assembly 23 carrying an appropriately aligned transducer array 20.

Figure 4:
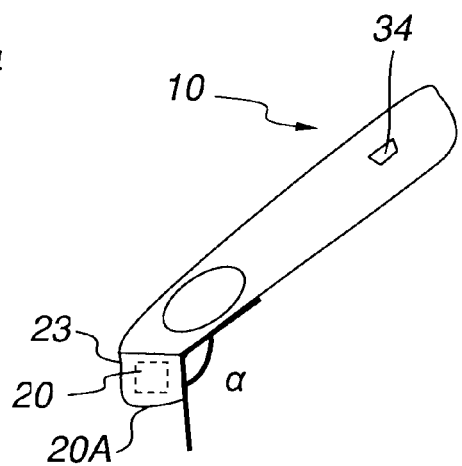
FIG. 4 shows a side view of the apparatus of FIG. 1 illustrating the angle between the transducer array and the housing.

In another embodiment, as shown in FIG. 4, the direction of output of sonic signals from transducer array 20 may be centered more or less at right angles to housing 12 (i.e. α is approximately 90°). In some embodiments, the direction of output of sonic signals from transducer array 20 may be centered at any angle in a range of 70° to 110° with respect to housing 12. With this configuration, housing 12 can be strapped or otherwise held against a subject such that the active face 20A of transducer array 20 is against the skin of the subject. In this configuration, device 10 can be used for monitoring physiological functions of the patient or monitoring the position of a device, such as a needle, or the like in the patient on a periodic, intermittent or continuous basis.

Figure 5:
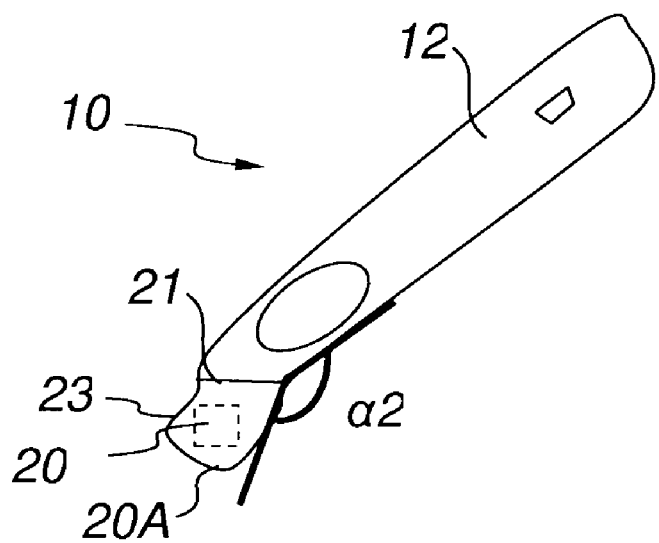
FIG. 5 shows a side view of the apparatus of FIG. 1 with the transducer array coupled to the housing by means of a flexible connector.

In some embodiments, the transducer assembly 23 comprises a flexible member connecting transducer array 20 to connector 21. The flexible member may, for example, comprise a flexible printed circuit board received in a flexible housing. In such embodiments a user may be able to bend the flexible housing to position transducer array 20 such that it forms a desired angle $\alpha_2$ relative to housing 12, as shown in FIG. 5.

A transducer array 20 typically has transducer elements that are arranged in a pattern having a longitudinal axis and a transverse axis. For example, the transducer elements may be arranged in a line, in which case, the longitudinal axis of transducer array 20 extends along the line and the transverse axis of transducer array 20 is perpendicular to the longitudinal axis. Typically the transducer array is longer than it is wide.

For certain ultrasound imaging operations it is desirable to scan the transducer array 20 over the surface of a subject in a direction such that the direction of scanning motion is generally parallel to the longitudinal axis of transducer array 20. In other imaging operations it is desirable to scan the transducer array 20 over the surface of the subject in a direction such that the direction of scanning is substantially perpendicular to the longitudinal axis of transducer array 20.

Figure 6:
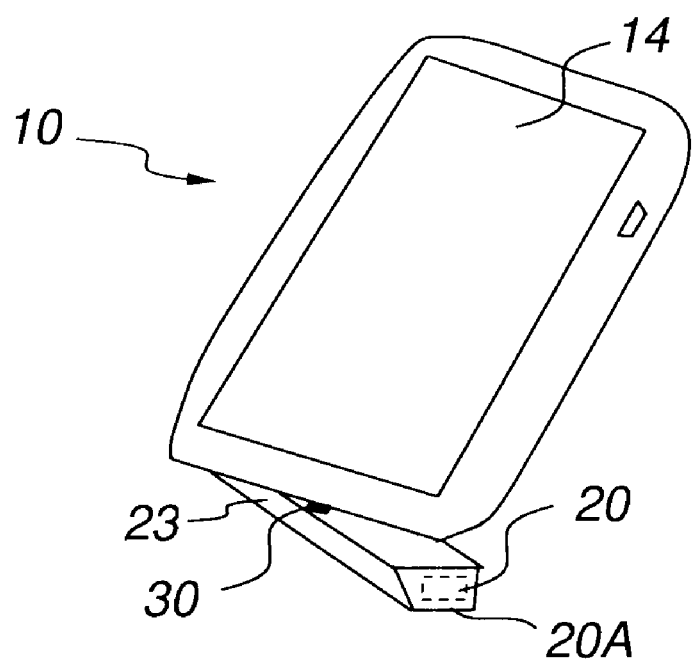
FIG. 6 shows the apparatus of FIG. 1 with the transducer array coupled to the housing by means of a pivotable swivel connector.

When scanning with a hand-held apparatus having a display 14, it is desirable that the operator be able to view the display 14 comfortably while the scanning is being performed. FIG. 6 shows an embodiment in which transducer array 20 is coupled to housing 12 by means which include a pivotable swivel connector 30. In the illustrated embodiment, pivotable swivel connector 30 permits pivotal motion of transducer array 20 about an axis that is substantially at right angles to active face 20A. In other embodiments, pivotable swivel connector 30 permits pivotal motion of transducer array 20 about an axis that is substantially perpendicular to one (or both) of the longitudinal and transverse axes of transducer array 20. The operator can pivot housing 12 relative to transducer array 20 so that display 14 can be seen clearly while the transducer array 20 is orientated appropriately for the current imaging operation.

In some embodiments, a transducer array 20 is both pivotable and replaceable. A pivotable swivel connector 30 or other pivoting means may be provided between transducer array 20 and connector 21 or between connector 22 and the rest of housing 12. Pivotal motion of transducer array 20 relative to housing 12 may optionally be limited to a particular angle, for example ±90° or ±70°, by the provision of suitable stops.

Figure 7:
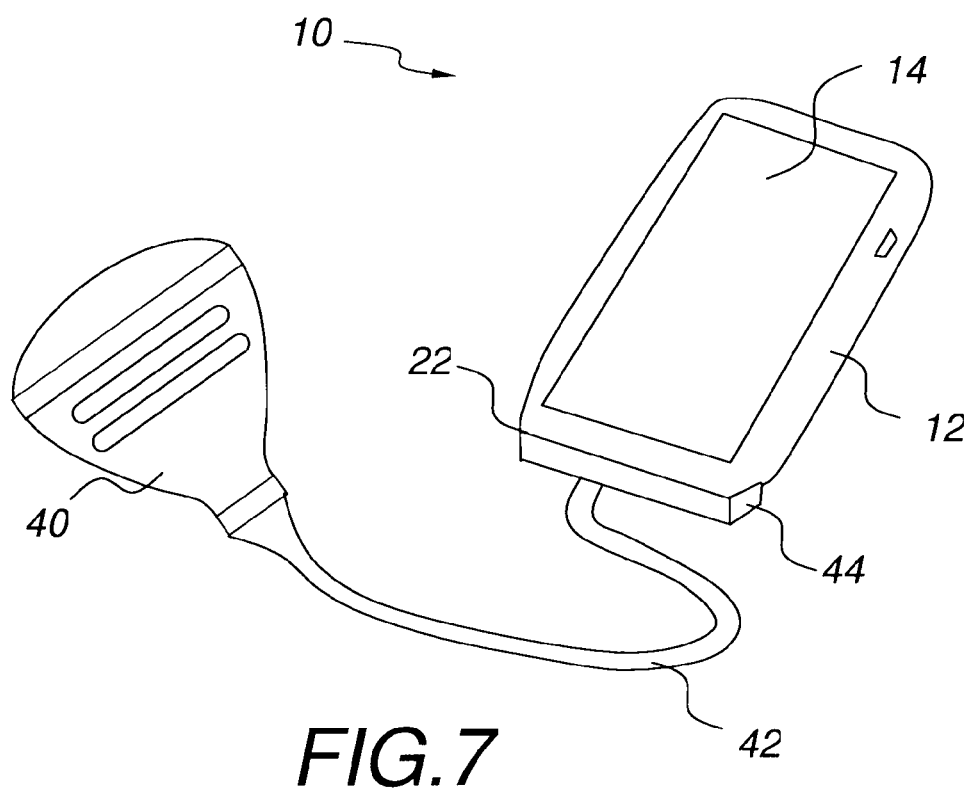
FIG. 7 shows a transducer array mounted to the housing by way of a short cable.
Figure 8:
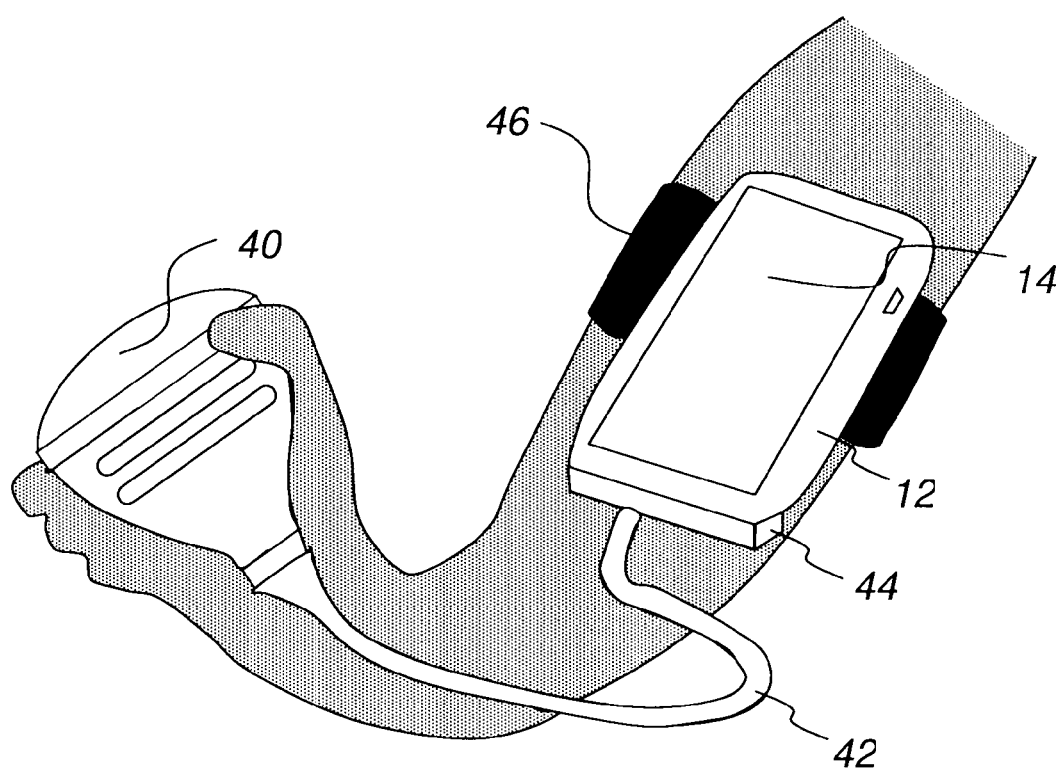
FIG. 8 shows the apparatus of FIG. 7 with a strap permitting the apparatus to be strapped to a user's arm.

FIG. 7 shows a hand-held imaging device according to a further example embodiment of the invention in which a transducer assembly 40 is mounted to device 10 by way of a short cable 42. Cable 42 comprises a connector 44 that plugs into connector 22 on housing 12. A strap 46 (see FIG. 8) may be provided to permit device 10 to be strapped to an operator's arm. This gives the operator full freedom to scan a transducer array carried by transducer assembly 40 over the subject while holding transducer assembly 40 at any desired angle to the surface of the subject's skin in any orientation, while still keeping display 14 in a position at which it can be clearly viewed and while leaving the operator's other hand free, as shown in FIG. 8.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. An ultrasonic imaging device comprising:
   a housing configured for holding in an operator's hand;
   a display disposed on a front face of the housing;
   an ultrasound transducer assembly coupled to the housing at a central location on an end of the housing adjacent to the front face, the ultrasound transducer assembly comprising a transducer array;
   wherein the transducer assembly is pivotally coupled to the housing for rotational motion of the transducer array with respect to the housing about a fixed axis, the transducer assembly is constrained against translational motion with respect to the housing, and the transducer assembly is pivotable to a configuration in which the transducer array lies along the end of the housing parallel to a plane of the display.

2. The ultrasonic imaging device according to claim 1 wherein the transducer assembly comprises a memory comprising configuration data for use in controlling one or more operational characteristics of the ultrasonic imaging device.

3. The ultrasonic imaging device according to claim 2 comprising a field-programmable gate array (FPGA) for controlling the transducer array, wherein the configuration data comprises configuration data for the FPGA.

4. The ultrasonic imaging device according to claim 1 wherein the transducer array is detachably coupled to the housing and is associated with a corresponding functional mode of operation of the ultrasonic imaging device and the ultrasonic imaging device is configured to automatically select the corresponding functional mode in response to detecting that the transducer array has been coupled to the housing.

5. The ultrasonic imaging device according to claim 4 wherein the ultrasonic imaging device is configured to automatically select the corresponding functional mode from among a plurality of possible operational modes in response to detecting that the transducer array has been coupled to the housing.

6. The ultrasonic imaging device according to claim 4 wherein the transducer assembly comprises a memory comprising configuration data defining the corresponding functional mode.

7. The ultrasonic imaging device according to claim 6 comprising a field-programmable gate array (FPGA) for controlling the transducer array, wherein the configuration data comprises configuration data for the FPGA.

8. The ultrasonic imaging device according to claim 4 wherein the transducer array comprises circuitry detectable by a controller of the ultrasonic imaging device to identify the transducer array.

9. The ultrasonic imaging device according to claim 1 comprising a plurality of transducer arrays wherein each one of the plurality of transducer arrays is detachably couplable to the housing.

10. The ultrasonic imaging device according to claim 1 wherein the transducer array is coupled to the housing by way of a connector and the transducer assembly comprises a flexible member coupling the transducer array to the connector, allowing the operator to bend the flexible member to achieve a desired angle between a central output direction of the transducer array and the housing.

11. The ultrasonic imaging device according to claim 1 wherein the pivotal coupling between the transducer assembly and the housing permits the pivotal motion of the transducer array relative to the housing about an axis which is perpendicular to an active face of the transducer array.

12. The ultrasonic imaging device according to claim 1 wherein the pivotal coupling between the transducer assembly and the housing permits the pivotal motion of the transducer array relative to the housing about axis which is perpendicular to at least one of a longitudinal axis of the transducer array and a transverse axis of the transducer array.

13. The ultrasonic imaging device according to claim 1 wherein the pivotal coupling between the transducer assembly and the housing permits the pivotal motion of the transducer array relative to the housing so as to allow the operator to maintain an orientation of the housing relative to the operator when changing between a scan direction parallel to a longitudinal axis of the transducer array and a scan direction perpendicular to the longitudinal axis of the transducer array.

14. The ultrasonic imaging device according to claim 1 comprising one or more stops disposed to limit the pivotal motion of the transducer assembly relative to the housing.

15. The ultrasonic imaging device according to claim 1 wherein the transducer array comprises at least one of: a transducer array having transducer elements arranged in a convex array, a transducer array having transducer elements arranged in a linear array, and a transducer array having transducer elements arranged to provide a phased array.

16. The ultrasonic imaging device according to claim 1, wherein the ultrasonic imaging device weighs less 10 pounds.

17. The ultrasonic imaging device according to claim 1, wherein the housing has a transverse dimension in a range of approximately 8 to 10 centimeters and a longitudinal dimension in a range of approximately 8 to 10 centimeters.

18. The ultrasonic imaging device according to claim 17, wherein the housing has a thickness of approximately 2 centimeters.

19. The ultrasonic imaging device according to claim 1 wherein the transducer assembly is detachably coupled to the housing.

* * * * *